United States Patent [19]

Saint et al.

[11] Patent Number: 4,682,034
[45] Date of Patent: Jul. 21, 1987

[54] BLAST WAVE DENSITOMETER SYSTEM

[75] Inventors: David H. Saint, Medicine Hat; John W. Funk, Vancouver, both of Canada

[73] Assignee: Her Majesty the Queen in right of Canada, Canada

[21] Appl. No.: 731,050

[22] Filed: May 6, 1985

[51] Int. Cl.$^4$ ............................................. G01N 23/08
[52] U.S. Cl. ............................... 250/363 R; 250/308; 250/338
[58] Field of Search ..................... 250/308, 369, 358.1, 250/256, 207, 363 R, 338 GA

[56] References Cited

U.S. PATENT DOCUMENTS

| | | | |
|---|---|---|---|
| 3,013,156 | 12/1961 | Hearn | 250/256 |
| 4,275,298 | 6/1981 | Wykes et al. | 250/367 |
| 4,292,522 | 9/1981 | Okumoto | 250/358.1 |
| 4,449,047 | 5/1984 | Monroe | 250/253 |

OTHER PUBLICATIONS

"Density Measurements in the Blast Wave from a Surface Burst 500 Ton TNT Hemispherical Charge", W. A. Anson and John M. Dewey, Suffield Technical Paper No. 305, Defence Research Establishment Suffield, Ralston, Alberta, Canada, Aug. 1965.
"Explosions in Air", Wilfred E. Baker, University of Texas Press, pp. 186–188, 1973.
"A System and Procedures for Measuring Blast Wave Density in a 500 Ton TNT Surface Burst", J. F. Ross, Suffield Technical Note No. 258, Defence Research Establishment Suffield, Ralston, Alberta, Canada, May, 1971.

Primary Examiner—Carolyn E. Fields
Attorney, Agent, or Firm—Stevens, Davis, Miller & Mosher

[57] ABSTRACT

A beta-attenuation densitometer is disclosed. The densitometer includes a source of beta radiation and a beta detector arranged to receive radiation from the source. The detector includes a scintillator that is caused to fluoresce by the radiation and a photomultiplier tube that detects the light emitted by the scintillator. The scintillator and photomultiplier are contained within a light-tight housing. Shock absorbing potting material protects the tube against damage.

10 Claims, 3 Drawing Figures

BLAST WAVE DENSITOMETER SYSTEM

FIELD OF THE INVENTION

The present invention relates to densitometers and more particularly to densitometers using the beta attenuation technique and suitable for measuring density in shock waves.

BACKGROUND

In a beta attenuation densitometer, a shock wave to be measured is passed between a radioactive source and a detector. The increase in density in the shock wave causes a decrease in the amount of radiation reaching the radiation detector. The detected radiation is converted to light in a scintillator crystal, and the light is converted to an electrical signal in a photomultiplier, the electrical signal becoming the system output.

Existing densitometers of the type in question have some deficiencies for use in high pressure shock waves because of the severe conditions encountered. The present invention aims at the provision of an improved densitometer for use in exceptionally severe conditions, including overpressures of up to 1040 kPa.

SUMMARY OF THE INVENTION

According to the present invention there is provided a densitometer comprising:
a source of beta radiation; and
a detector including
(a) a housing spaced from the source of beta radiation;
(b) a scintillator mounted in the housing to receive radiation from the beta radiation source;
(c) a light seal over the scintillator for preventing ambient light from entering the scintillator while passing beta radiation from the source to the scintillator;
(d) a photomultiplier tube in the housing to receive light emitted by the scintillator, the photomultiplier tube having electrical connection pins thereon;
(e) electrical means mounted on the pins of the photomultiplier tube; and
(f) an elastomeric potting compound, opaque to ambient light, securing the photomultiplier tube and the electrical means in the housing with the tube out of contact with the housing.

The isolation of the photomultiplier tube from the housing through the medium of an elastomeric potting compoind significantly improves the shock resistance of the densitometer. In preferred embodiments, the housing is also mounted with an elastomeric shock mounting.

In preferred embodiments, improvements are provided in the light seal, the geometry of the radiation source and electromagnetic shielding.

Because the output of the photomultiplier is non-linear, the preferred embodiment also includes a non-linear amplifier that compensates for the non-linearity and produces a densitometer output that is linear with respect to the density being measured.

BRIEF DESCRIPTION OF THE DRAWINGS

In the accompanying drawings, which illustrate exemplary embodiments of the present invention.

DETAILED DESCRIPTION

Figure 1:
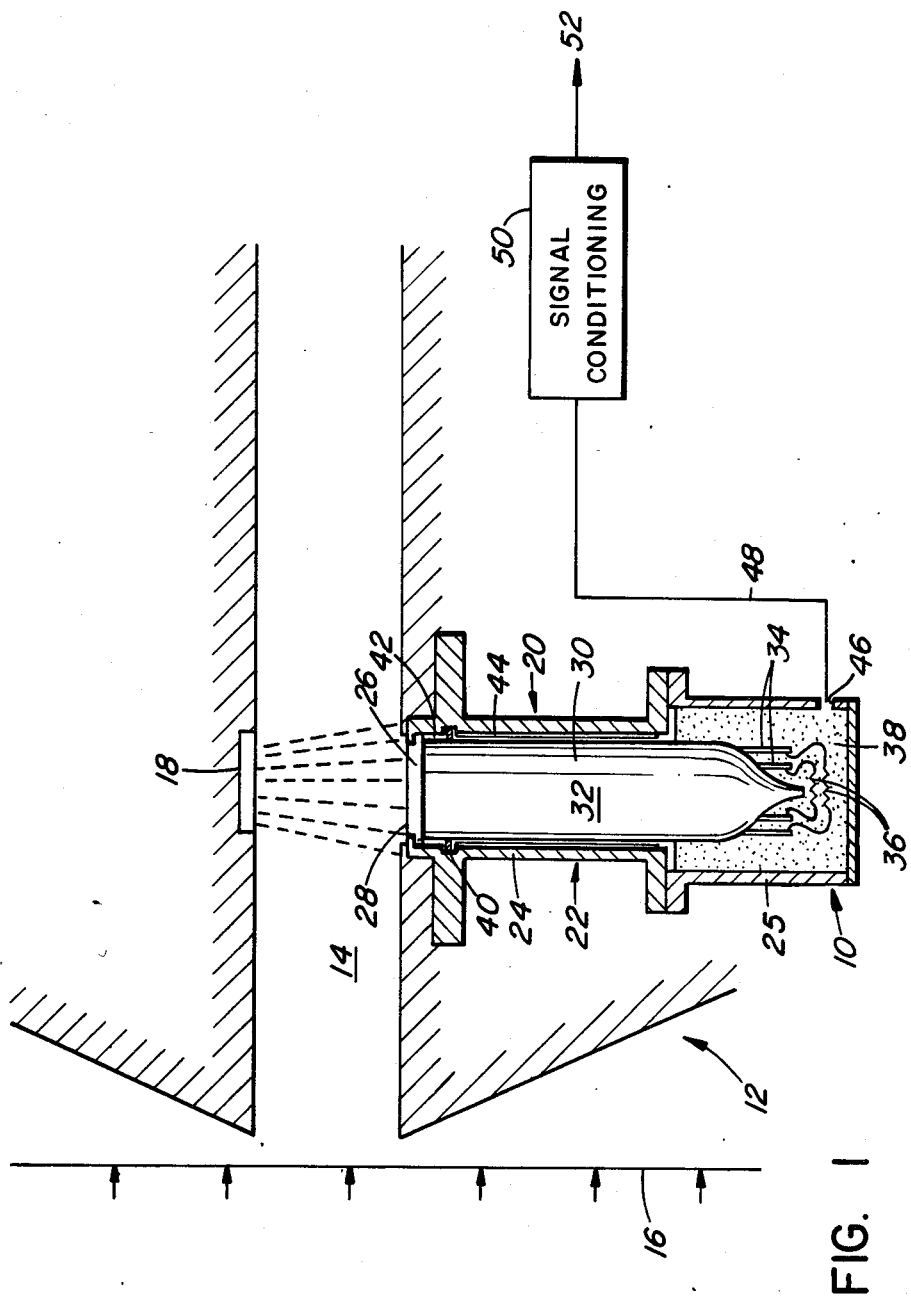
FIG. 1 is a schematic diagram, partially in cross section, of one embodiment of the present densitometer mounted in a blast gauge.

Turning to the drawings, and most particularly to FIG. 1, there is illustrated a densitometer 10 mounted in a blast gauge 12. The blast gauge has a central passage 14 through which a shock wave 16 is propagated. On one side of the passage 14 is a circular radioactive source of beta radiation 18. On the opposite side of the passage is a beta detector 20. The detector 20 includes a housing 22 with a top section 24 and a bottom section 25. The top converts the light into electrical energy. The illustrated tube section 24 contains a circular scintillator 26 that confronts the radioactive source 18 so that the beta radiation emitted from the source 18 impinges on the scintillator 26. The scintillator is equipped with a light seal 28 to prevent its activation by ambient light. In this embodiment, the light seal 28 is an aluminized polyester film sold under the Trade Mark Mylar adhered to the surface of the scintillator 26. The film is covered with a thin coat of black paint and an acrylic material to provide several layers which may be abraded away before the Mylar light shield is damaged. This is particularly useful under dusty conditions.

In this embodiment, the scintillator is europium activated calcium fluride. The beta radiation entering the scintillator 26 causes the scintillator to fluoresce. The visible light emitted by the scintillator is passed into a photomultiplier tube 30 mounted in the housing adjacent the scintillator. The photomultiplier tube in this embodiment is a KM2946 with a glass envelope 32 and connector pins 34 mounted directly on the envelope. The low noise resistors 36 that make up a dynode divider chain are directly soldered to the pins 34. The leads from the dynode chain are "Mil-Crimped" to provide strain relief.

The bottom end of the tube 30 is potted in the lower housing part 25 with an elastomeric potting compound 38. This provides a shock resistant mounting for the tube in the housing. The elastomer is opaque to prevent light leakage through the elastomer into the tube. At the upper end of the tube is an O-ring 40 that aligns the tube in the upper part of the housing 24. The O-ring 40 also provides a closed chamber bounded by the tube, the housing and the scintillator 26 that is filled with a high viscosity optical coupling fluid that provides both optimum light transmission as well as vibration isolation from the scintillator.

The tube 30 is surrounded by an electromagnetic shield 44.

The housing 20 has an opening 46 adjacent the bottom through which the leads 48 from the tube pass. The leads go to a signal conditioning circuit 50 that is non-linear to match the non-linearity of the tube output with respect to density in the passage 14, thus yielding a linear output 52.

Figure 2:
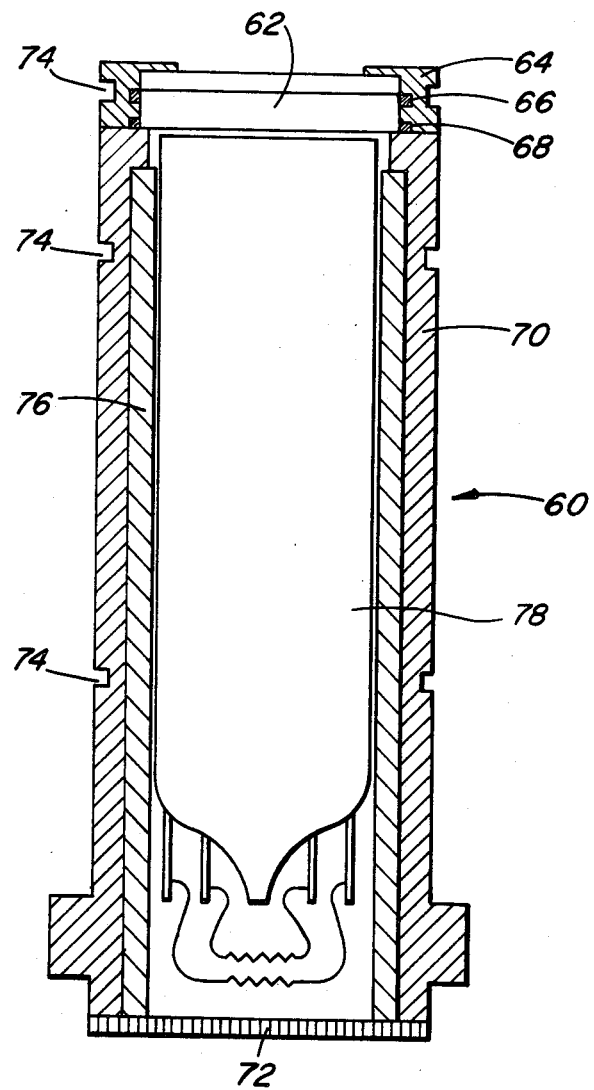
FIG. 2 is an elevation, partially in cross section, of an alternative embodiment of the densitometer.

An alternative embodiment of the detector, designated 60, is illustrated in FIG. 2. The scintillator 62 is removably mounted on the housing 70 by means of scintillator ring 64 fastened to the top of the housing by machine screws (not illustrated). O-ring seals 66 and 68 ensure a light tight seal between the scintillator, the scintillator ring 64 and the housing 70. The housing 70 is in this embodiment made in one part, generally in the configuration of a tube with a bottom cover 72. The scintillator ring 64 and the housing 70 are equipped with O-ring grooves 74 in their outer surfaces. These accommodate resilient O-rings for mounting the housing, for example in a blast gauge. The electromagnetic shield 76 in this embodiment is a thicker cylinder of high permeability shielding material to provide an improved magnetic shielding capability for certain applications. The photomultiplier tube 78 is mounted in the housing in the same way as in the embodiment of FIG. 1.

Figure 3:
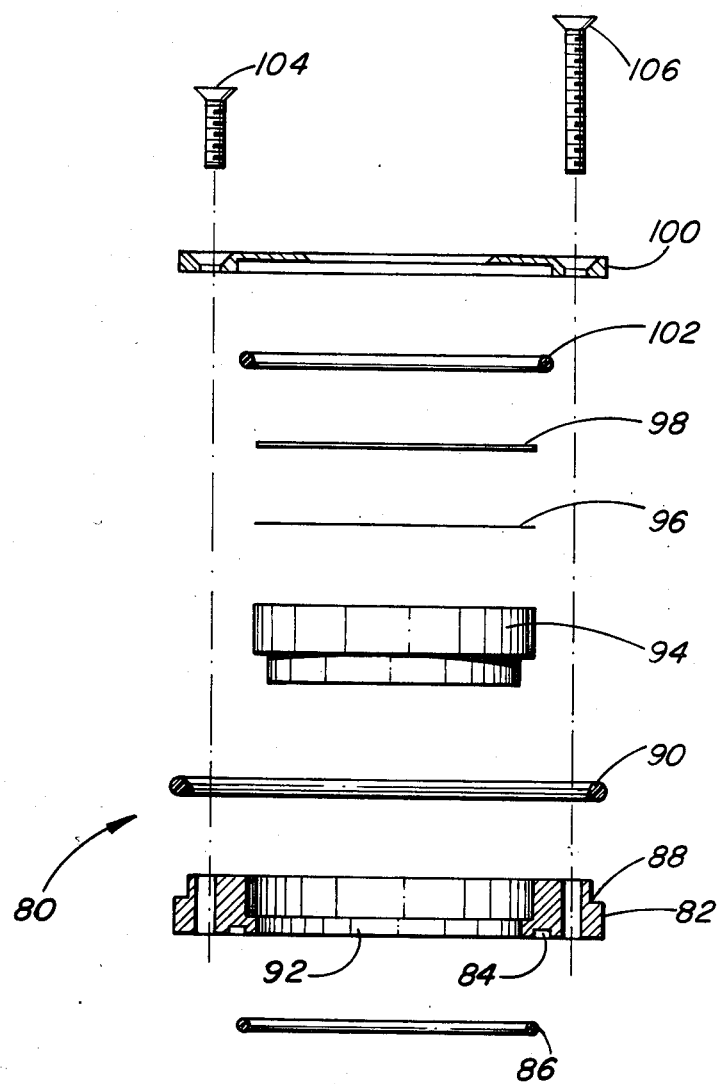
FIG. 3 is anexploded view of an alternative light seal assembly.

FIG. 3 illustrates an alternative form of light seal for use in the embodiment of FIG. 2. In this embodiment, the scintillator and scintillator ring assemblies are replaced with an alternative assembly that accommodates a metal foil light seal. As illustrated in the drawing, the assembly 80 includes a scintillator ring 82 with an O-ring groove 84 in its bottom surface to accommodate an O-ring 86. The peripheral surface of the ring 82 is at 88 to accommodate an O-ring 90 analogous to the ring 66 of the embodiment of FIG. 2. The ring 82 has a stepped internal bore 92 that accommodates a scintillator 94 with a similarly stepped outer periphery shape. A metal foil light seal 96 is positioned over the scintillator 94. A gasket 98 engages the top surface of the foil 96 around its periphery to seal the foil against the underside of a ring cover 100. The ring cover 100 is sealed to the scintillator ring 82 by an internal O-ring 102. The complete assembly is held in place on the detectors by two cap screws 104 and 106.

In an alternative embodiment of the detector, not illustrated in the accompanying drawings, the light seal is a vacuum deposited metal layer on the surface of the scintillator. For such an embodiment, the scintillator must be a hard crystal, while in other embodiments organic scintillators can be used.

The embodiment of the invention in which an exclusive property or privilege is claimed are defined as follows:

1. A densitometer comprising:
   a source of beta radiation
   a detector including
   (a) a housing spaced from the source of beta radiation;
   (b) a scintillator mounted in the housing to receive radiation from the beta radiation source;
   (c) an abrasion resistant light seal over the scintillator for preventing ambient light from entering the scintillator while passing beta radiation from the source to the scintillator;
   (d) a photomultiplier tube in the housing to receive light emitted by the scintillator, the photomultiplier tube having a glass envelope and electrical connection pins secured directly to the envelope at a base end thereof;
   (e) a dynode divider chain mounted directly on the pins of the photomultiplier tube;
   (f) an elastomeric potting compound, opaque to ambient light, securing the base end of the photomultiplier tube envelope, the electrical connection pins and the dynode divider chain within and out of contact with the housing; and
   (g) an O-ring around the photomultiplier tube envelope, centering the tube in the housing.

2. A densitometer according to claim 1, further including an electromagnetic shield surrounding the photomultiplier tube, within the housing.

3. A densitometer according to claim 1, wherein the scintillator and the radiation source are substantially circular.

4. A densitometer according to claim 1, wherein the scintillator comprises europium activated calcium fluoride.

5. A densitometer according to claim 1, including elastomeric means for mounting the housing in a gauge.

6. A densitometer according to claim 1, further including a non-linear signal conditioning circuit external to said housing and having an input connected to said photomultiplier tube and an output, the characteristics of the amplifier being such that the signal conditioning circuit output is a linear function of the amount of beta radiation reaching the scintillator from the source of beta radiation.

7. A densitometer according to claim 1, wherein the light seal comprises an aluminized polyester film adhered to the scintillator.

8. A densitometor according to claim 7, wherein the scintillator is an organic material.

9. A densitometer according to claim 1, wherein the scintillator is a hard crystal.

10. A densitometer accordng to claim 9, wherein the light seal comprises a layer of metal vacuum deposited on to the surface of the scintillator.

* * * * *